United States Patent [19]

Lambert

[11] Patent Number: 5,163,908
[45] Date of Patent: Nov. 17, 1992

[54] FAIL SAFE COMPOSITE HYPODERMIC SYRINGE WITH REVERSIBLE NEEDLE AND GUARD ASSEMBLY

[76] Inventor: William S. Lambert, 52 Tokalon Pl., Metairie, La. 70001

[21] Appl. No.: 605,153

[22] Filed: Oct. 29, 1990

Related U.S. Application Data

[63] Continuation-in-part of Ser. No. 422,771, Oct. 16, 1989, abandoned.

[51] Int. Cl.[5] ............................................. A61M 5/50
[52] U.S. Cl. .................................. 604/110; 604/198; 604/241
[58] Field of Search ............... 604/110, 192–198, 604/187, 265, 263, 239–243

[56] References Cited

U.S. PATENT DOCUMENTS

| | | | |
|---|---|---|---|
| 3,354,881 | 11/1967 | Bloch | 604/198 |
| 4,392,859 | 7/1983 | Dent | 604/198 |
| 4,564,054 | 1/1986 | Gustausson | 141/329 |
| 4,666,436 | 5/1987 | McDonald et al. | 604/198 |
| 4,743,233 | 10/1988 | Schneider | 604/192 |
| 4,775,363 | 10/1988 | Sandsdalen | 604/110 |
| 4,795,432 | 1/1989 | Karczmer | 604/110 |
| 4,804,371 | 2/1989 | Vaillancourt | 604/198 |
| 4,919,652 | 4/1990 | Alter et al. | 604/110 |
| 4,950,250 | 8/1990 | Haber et al. | 604/192 |
| 4,968,304 | 11/1990 | Alter et al. | 604/192 |

FOREIGN PATENT DOCUMENTS

| | | | |
|---|---|---|---|
| 0308380 | 3/1989 | European Pat. Off. | 604/110 |
| 8911304 | 11/1989 | PCT Int'l Appl. | 604/198 |

*Primary Examiner*—John D. Yasko
*Assistant Examiner*—Adam J. Cermak

[57] ABSTRACT

A disposable hypodermic syringe with collapsible plunger has a needle guard filled with a disinfectant-saturated media. The guard is threadably-reversibly mountable, end-for-end, on a distal end of the syringe barrel.

1 Claim, 1 Drawing Sheet

FAIL SAFE COMPOSITE HYPODERMIC SYRINGE WITH REVERSIBLE NEEDLE AND GUARD ASSEMBLY

CROSS REFERENCE TO RELATED APPLICATIONS

This application is a continuation-in-part of my co-pending application Ser. No. 07/422,771, filed on Oct. 16, 1989, now abandoned.

BACKGROUND OF THE INVENTION

1. Field of the Invention

This invention relates to medical equipment, and more particularly to disposable hypodermic needles.

2. Description of the Prior Art

International law applicable to construction-specification of disposable hypodermic syringes does not exist to mandate construction criteria for an absolute on-use limitation. Syringe/needle-sharing among drug-users is fueling ravishing disease-spread. Accidental-sticks to World Health Care personnel have spread infection alarmingly. It has been a long-existing goal of syringe designers to create a disposable syringe which will minimize exposure of an infected needle and help prevent transmittal of often fatal diseases.

A tubular serum reservoir is traditionally made of extruded polymeric plastic. It is closed at lower end by a bulkhead, which has an opening to allow serum infusion/discharge. Totally open at the grippable upper-end, it receives a sliding, fluid-tight plunger, which forces medicine out through a needle and which creates internal vacuum when moved outwardly.

Some of the known devices provide for the use of sheaths, or sleeves which enclose the needle, or a needle tip during non-use. Some of the devices suggest the use of collapsible sleeves to permit injection. Still others teach the use of self-destructing syringes. However, none of the known devices provides for the use of a disposable syringe having means for disinfecting an injection site during the process of injection, with the piston being designed to collapse and prevent re-use of the syringe. Additionally, many known devices are complicated to manufacture, often inconvenient and unreliable in use and do not afford total sterility of the needle.

SUMMARY OF THE INVENTION

It is therefore an object of the present invention to provide a disposable hypodermic syringe having disinfectant means.

It is another object of the present invention to provide a hypodermic syringe having means for covering the needle when not used.

It is a further object of the present invention to provide a hypodermic syringe having means for irreversible destructing a plunger.

It is still further object of the present invention to provide a disposable hypodermic syringe which is easy to use and inexpensive to manufacture.

These and other objects are achieved through provision of a syringe having a piston slidably movable within a syringe barrel and contacting the syringe barrel distal and the piston assembly includes means for destructing the piston and causing collapse of the piston when the piston strikes the barrel distal end. A needle guard encloses the needle and moves in a telescopic relationship thereto. The guard is entirely filled with a disinfectant saturated sponge type media for simultaneous disinfecting of an injection site. The guard is screwably-reversibly mounted end-for-end, on the distal end of the syringe barrel.

DETAIL DESCRIPTION OF THE PREFERRED EMBODIMENT

Figure 3C:
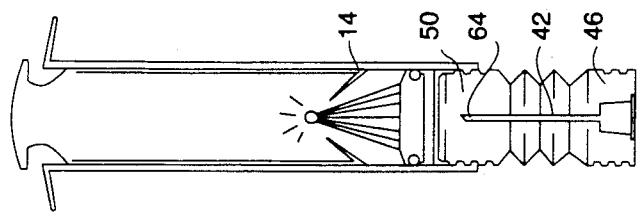
FIG. 3C is a schematic view illustrating reverse attachment of the needle/guard assembly.

The syringe 1 of the present invention comprises an elongated plunger 10 which is telescopically slidably engaged in a syringe barrel, or medicine reservoir 20. A distal end 12 of the plunger 10 is radially cut into a plurality of segments 14 which are in a tight contact with each other when the syringe 1 is not in use or when the plunger 10 is moved outwardly, such as for drawing of medicine.

A central opening 16 is formed in the end 12 to receive a support 18 of a ball-shaped end 22 of a conical plunger destructing means 24. The fluted cone 24 is fixedly attached and rides with a piston 30 which contacts the interior walls of the syringe barrel 20 in a fluid-tight engagement.

An O-ring 32 seals the contact area, although it is envisioned that some of the embodiments can be manufactured without the sealing O-ring 32. The surface of the piston 30 opposite the cone 24 strikes an inner end of a needle and guard assembly 40 when moving to expel medicine from the syringe barrel 20.

The needle and guard assembly 40 comprises a needle 42 which is secured within an enclosing needle guard 44. The guard 44 has a first end portion 46, an accordion-like middle portion 48 and a second end portion 50.

The end portions 46 and 50 are provided with external threads 52 and 54, respectively.

The inner wall of the barrel 20 is provided with matching threads, as at 56, to threadably engage the threads 52 or 54, interchangeably. The guard 44 is entirely filled with disinfectant-saturated sponge-type porous media, which when compressed, releases the disinfectant to the area surrounding an injection site, thereby eliminating the necessity to provisionally disinfect the site before injecting the needle into a body tissue of a patient.

The needle and guard assembly 40 is enclosed in its entirety in a flexible plastic-like cover which prevents evaporation of the disinfectant. The cover is perforated as at 60 to allow removal of the cover immediately prior to injection.

The foam-like medium of the guard 44 is strong enough to allow threading-in of the needle base 62 in the end portion 46, but still flexible and deformable enough to allow contraction of the guard 44 to expose a pointed tip 64 of the needle 42 and draw medicine or perform an injection.

In its extended position the guard 44 entirely encompasses the needle 42 and retains it in a sterile environment. The piston 30 at that time is adjacent to the "bulkhead" surface of the end portion 46. The plunger 10 supports the cone 24 by engaging in the ball 22, while the cone 24, being fixedly attached to the piston 30, forces the piston 30 to move along when drawing of medicine, and thereby permit creation of the necessary vacuum, when the plunger 10 is moved outwardly for the barrel 20 to a position shown in FIG. 3A.

In operation, the user removes the cover from the guard 44 by tearing the cover along the perforation line 60. The pointed tip 64 of the needle 42 becomes exposed when the guard 44 is compressed slightly and is allowed to enter a medicine bottle to draw the medicine.

Figure 3B:
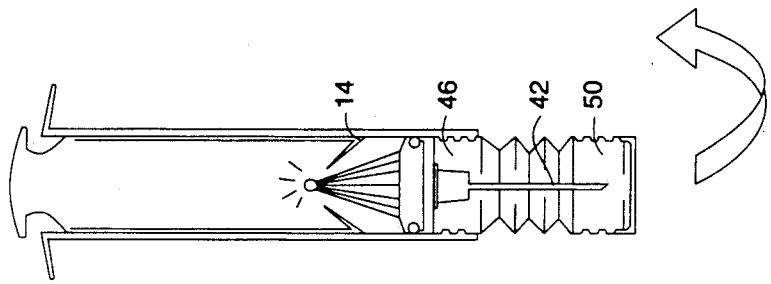
FIG. 3B is a schematic view illustrating destruction of the plunger.
Figure 3A:
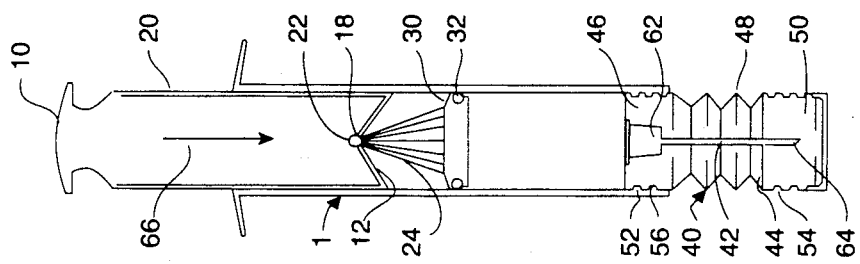
FIG. 3A is a schematic view illustrating downward movement of the plunger.
Figure 2:
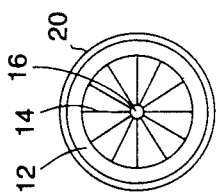
FIG. 2 is a bottom view of the plunger destructing means.
Figure 1:
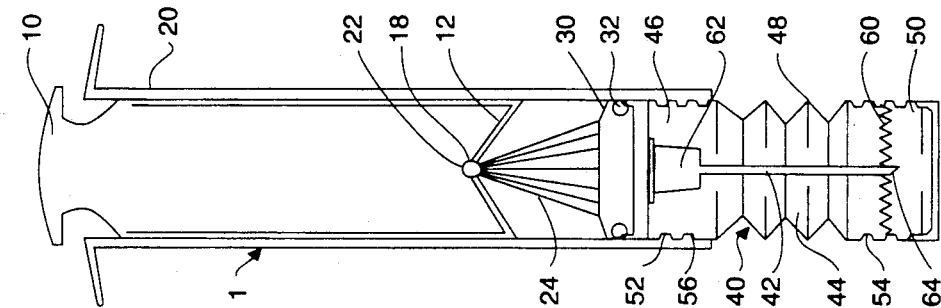
FIG. 1 is a plan view in accordance with the present invention.

During injection, the plunger 10 is forced to move in the direction of arrow 66 in FIG. 3A and strike with the piston 30 against the end portion 46. The guard 44 is compressed to expose the tip 64 and allow the needle to enter a body tissue of patient. The disinfectant is released to clean the injection site.

At the same time, the distal end 12 of the plunger 10 permanently collapses, since the plunger 10 is forcefully moved inwardly towards the barrel distal end, and the fluted cone 24 is forced to break the end 12 into a plurality of separate segments 14, as illustrated in FIG. 3B. The syringe 1 cannot be re-used, since the piston 30 cannot be moved again to create vacuum due to the fact that it is no longer attached to the slidable plunger 10.

After the injection is completed, the needle and guard assembly 40 is disengaged from the barrel 20 and turned over to allow the end portion 50 to be threadably engaged end-for-end with the distal end of the barrel 20, as illustrated in FIG. 3C. During these steps the needle 42 remains covered at all times due to extension of the flexible medium of the guard 44 back to its original pre-deformation size. Thereby, the dange of accidental stick by medical personnel is prevented.

The syringe plunger 10, the barrel 20, cone 24, and piston 30 can be constructed from any of the number of plastic materials. The medium filled with disinfectant substance can be made from flexible, deformable porous material, such as foam.

DRAWING REFERENCE NUMERALS 1 syringe ensemble
10 male plunger/shaft
12 distal end of plunger/shaft 10
14 fracturable preslices at end-face 12 of 10
16 entry aperture of receive ball-shaped 22
18 support for 22
20 female housing/serum reservoir
22 retainer ball-shape atop cone 24 thru-aperture 16
24 destructor (of 14)-cone/piston
30 piston
32 seal-area of 30—O-ring therefor optional
40 needle-module complete - including needle 42/guard 44
42 concentrically-cast/embedded Standard needle
44 formed disinfectant/foam-sponge media
46 1st end-portion of 40
48 accordion-like middle portion of 40
50 2nd end-portion of 40
52 external threading of 46, matching 56
54 external threading of 50, matching 56
56 threaded inner-wall of 20, receivable of 52/54
60 perforation line at 50
62 needle base of 42 as embedded in 46
64 needle tip
66 direction arrow

I claim:
1. A hypodermic syringe, comprising:
a syringe barrel, a piston means slidable within the barrel and being permanently collapsible upon striking a distal end of the syringe barrel, a telescopic needle and guard assembly, the guard movable between an extended position entirely encompassing the needle and a contracted position exposing a pointed tip of the needle, the guard being entirely filled with a disinfectant-saturated porous media, the guard being threadably-reversibly mountable, end-for-end, on the distal end of the syringe.

* * * * *